United States Patent
Milano et al.

(10) Patent No.: US 9,486,317 B2
(45) Date of Patent: *Nov. 8, 2016

(54) METHOD OF ARTHROSCOPIC OSTEOCHONDRAL RESURFACING USING PRP STRENGTHENED WITH FIBRIN GLUE

(75) Inventors: Giuseppe Milano, Rome (IT); Gerlinde Michel, Munich (DE); Stephane Naudin, Planegg (DE); Hans Linden, Köln (DE); Reinhold Schmieding, Naples, FL (US)

(73) Assignee: Arthrex Inc., Naples, FL (US)

( * ) Notice: Subject to any disclaimer, the term of this patent is extended or adjusted under 35 U.S.C. 154(b) by 1109 days.

This patent is subject to a terminal disclaimer.

(21) Appl. No.: 12/198,836

(22) Filed: Aug. 26, 2008

(65) Prior Publication Data

US 2009/0062870 A1   Mar. 5, 2009

Related U.S. Application Data

(60) Provisional application No. 60/968,272, filed on Aug. 27, 2007.

(51) Int. Cl.

| | |
|---|---|
| *A61F 2/02* | (2006.01) |
| *A61K 35/16* | (2015.01) |
| *A61K 35/14* | (2015.01) |
| *A61K 35/28* | (2015.01) |
| *A61F 2/30* | (2006.01) |
| *A61B 17/00* | (2006.01) |
| *A61B 17/56* | (2006.01) |

(52) U.S. Cl.
CPC ..... *A61F 2/30756* (2013.01); *A61B 17/00491* (2013.01); *A61B 2017/00495* (2013.01); *A61B 2017/564* (2013.01); *A61F 2002/30757* (2013.01); *A61F 2002/30761* (2013.01); *A61F 2310/00377* (2013.01)

(58) Field of Classification Search
None
See application file for complete search history.

(56) References Cited

U.S. PATENT DOCUMENTS

| | | | | |
|---|---|---|---|---|
| 6,723,131 | B2 * | 4/2004 | Muschler | 623/23.51 |
| 7,229,959 | B1 * | 6/2007 | Drohan et al. | 514/2.4 |
| 2003/0212426 | A1 * | 11/2003 | Olson et al. | 606/191 |
| 2005/0038520 | A1 * | 2/2005 | Binette et al. | 623/18.11 |
| 2006/0190078 | A1 * | 8/2006 | Fell | 623/14.12 |

OTHER PUBLICATIONS

Thompson, D.F.; Letassy, N.A.; Thompson, G.D. Fibrin glue: a review of its preparation, efficacy, and adverse effects as a topical hemostat. The Annals of Pharmacotheraphy. Drug Intelligence & Clinical Pharmacy: vol. 22, No. 12, pp. 946-952, 1998. http://www.theannals.com/cgi/content/abstract/22/12/946 Reviewed on Jun. 15, 2011.*
Petersen et al. Tissue adhesives and fibrin glues. Gastrointestinal Endoscopy, 2004, vol. 60, No. 3, p. 327-333.*
http://www.merriam-webster.com/dictionary/resilient referenced on Jul. 7, 2016.*

* cited by examiner

*Primary Examiner* — Jessica Worsham
(74) *Attorney, Agent, or Firm* — McDonnell Boehnen Hulbert & Berghoff LLP

(57) ABSTRACT

Methods of arthroscopic resurfacing of a joint utilizing a biological component strengthened with fibrin glue. The biological component is selected from the group consisting of PRP, bone marrow aspirate (BMA) and autologous conditioned plasma (ACP). The biological component/fibrin glue composition may be inserted (by injection or by employing a biologic resurfacing mold, for example) into a transosseous tunnel in the vicinity of the defect to be repaired. Upon insertion at the defect site, the biological component/fibrin glue composition is designed to coagulate and solidify within few minutes, to advance the healing of the damaged tissue and tissue growth. The biological component/fibrin glue composition may optionally comprise components such as growth factors, antiseptic chemicals and/or antibiotics and/or electrolytes, or hormones or site-specific hybrid proteins, among others.

16 Claims, 4 Drawing Sheets

METHOD OF ARTHROSCOPIC OSTEOCHONDRAL RESURFACING USING PRP STRENGTHENED WITH FIBRIN GLUE

CROSS-REFERENCE TO RELATED APPLICATIONS

This application claims the benefit of U.S. Provisional Application No. 60/968,272, filed Aug. 27, 2007, the entire disclosure of which is incorporated by reference herein.

FIELD OF THE INVENTION

The present invention relates to a surgical method for resurfacing bone defects using a biological compound comprising platelet-rich plasma (PRP) and fibrin glue.

BACKGROUND OF THE INVENTION

Joint injuries typically involve damage to the bones and/or tendons that form the joint. This damage can range from bone chips to tears to simple wear. In the case of bone chips or wear, it is often necessary to repair the damage by replacing the missing bone material. This has been typically accomplished by attaching an implant over the defect that replicates the original bone structure.

A promising method of repairing bone damage is the use of platelet-rich plasma (PRP). PRP is obtained from the blood of blood donors. Previous studies have mixed PRP with a demineralized bone matrix, placed the resulting compound in a capsule, and then inserted the capsule near the bone in need of repair. Unfortunately, these studies have found the process to be largely unsuccessful at rebuilding bone structure.

BRIEF SUMMARY OF THE INVENTION

The present invention relates to methods of arthroscopic resurfacing of a joint utilizing a biological component strengthened with fibrin glue. The biological component is selected from the group consisting of PRP, bone marrow aspirate (BMA) and autologous conditioned plasma (ACP). The biological component/fibrin glue composition may be inserted (by injection or by employing a biologic resurfacing mold, for example) in the vicinity of the defect to be repaired. Upon insertion at the defect site, the biological component/fibrin glue composition is designed to coagulate and solidify within few minutes, to advance the healing of the damaged tissue and tissue growth.

Other features and advantages of the present invention will become apparent from the following description of the invention, which refers to the accompanying drawings.

DETAILED DESCRIPTION OF THE INVENTION

Figure 1:
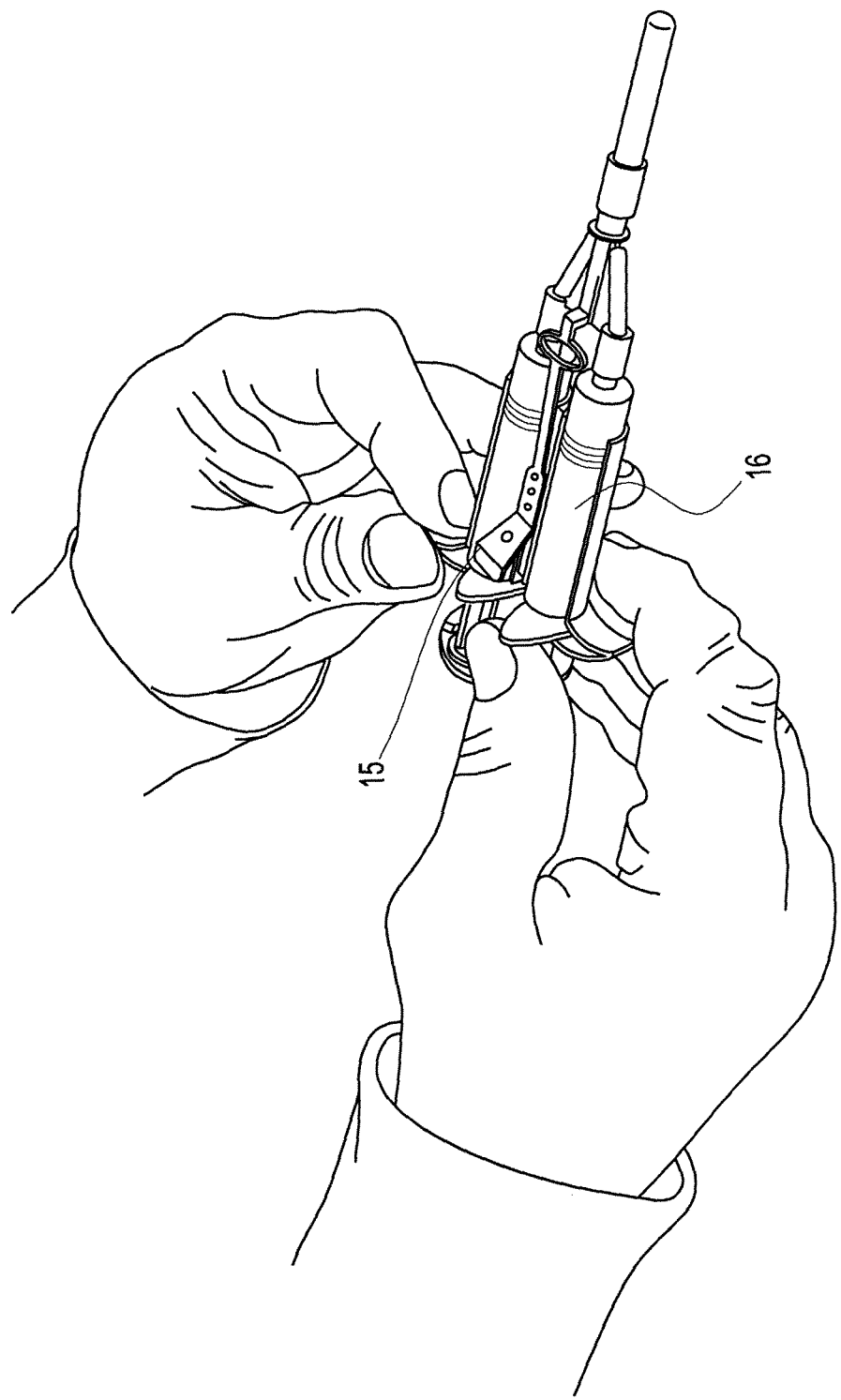
FIG. 1 illustrates a prepackaged, ready-to-use Fibrin glue for obtaining a biological component/fibrin glue composition in accordance with an embodiment of the present invention.

The examples provided below detail the preferred embodiments of the present invention. Other features, embodiments, and advantages of the invention beyond those discussed in the detailed description will be obvious to those skilled in the art. Those skilled in the art should appreciate that many changes may be made to the present invention without departing from the scope or spirit of the present invention.

The present invention relates to methods of arthroscopic resurfacing of a joint utilizing a biological component (selected from the group consisting of PRP, ACP and BMA) strengthened with fibrin glue. The biological component/fibrin glue composition may be optionally employed in conjunction with a biologic resurfacing mold (for example, a metal or plastic cap or an implant) provided with at least one channel, slot or inner hole through which the biological component/fibrin glue composition may be injected at the repair site. Once the biological component/fibrin glue composition has sufficiently coagulated and solidified, the biologic resurfacing mold may be removed and the process may be repeated at the location of other defects.

In an exemplary embodiment, the present invention provides a PRP/fibrin glue composition or PRP/fibrin glue "cocktail," which is a stable biological compound that can be injected into a transosseous tunnel (for example, tibial or femoral tunnel), in the vicinity of the defect to be repaired, and that can be further forced under pressure to securely contact the defect. Upon insertion at the defect site, the PRP/fibrin glue composition is designed to coagulate and solidify within few minutes, to advance the healing of the damaged tissue and tissue growth. Preferably, the PRP/fibrin glue composition is an autogenous PRP/fibrin glue composition.

The PRP/fibrin glue composition may be optionally employed in conjunction with a biologic resurfacing mold (for example, a metal or plastic cap or an implant) provided with at least one channel, slot or inner hole through which the PRP/fibrin glue composition may be injected at the repair site. Once the PRP/fibrin glue composition has sufficiently coagulated and solidified, the biologic resurfacing mold may be removed and the process may be repeated at the location of other defects.

The present invention also provides a method of enhancing the healing of damaged tissue at an arthroscopic resurfaced site. The method comprises the steps of: (i) providing a mixture of a biological component (selected from the group consisting of PRP, ACP and BMA) and fibrin glue; (ii) injecting the biological component/fibrin glue mixture through an arthroscopic portal at the defect site (arthroscopic resurfaced site); and (iii) optionally solidifying the biological component/fibrin glue mixture.

In another exemplary embodiment, the present invention provides a method of repairing bone damage by: (i) providing a mixture comprising PRP and fibrin glue; (ii) injecting the PRP/fibrin glue mixture through an arthroscopic portal and through a prepared osteochondral socket, at the defect site (i.e., the arthroscopic resurfaced site); and (iii) optionally solidifying the PRP/fibrin glue mixture. The step of injecting the PRP/fibrin glue mixture through the arthroscopic portal may further and optionally comprise the steps of: providing a biologic resurfacing mold (for example, a cap or a clear, plastic umbrella) over the prepared osteochondral socket; expanding the mold to fully cover the diameter of the osteochondral socket; and injecting the PRP/fibrin glue mixture through at least a channel, passage or slot provided within the mold.

The PRP/fibrin glue composition or "cocktail" of the present invention is preferably an autogenous PRP/fibrin glue composition which may optionally comprise additional components such as BMA, ACP, growth factors, additional antiseptic chemicals and/or antibiotics and/or electrolytes, or hormones or site-specific hybrid proteins (that promote or enhance the wound healing effectiveness of the growth factors), among others.

Growth factors may comprise proteinaceous factors, for example, which play a role in the induction or conduction of growth of tissue, ligaments, bone, cartilage or other tissues associated with bone or joints. In particular, the following growth factors contained in platelets are set forth below (and their effects):

PDGF (Platelet-derived growth factor)—Stimulates collagen synthesis, the formation of blood vessels and fibroblast proliferation; activation of macrophages and neutrophiles; activates TGF-β; attracts stem cells.

FGF (Fibroblast growth factor)—Stimulates the formation of blood vessels, collagen synthesis, wound contraction, matrix synthesis, epithelialisation.

TGF-β (Transforming growth factor β)—Reduces scar formation; reduces wound healing disturbances caused by corticoids; attracts fibroblasts and promotes their proliferation; stimulates collagen synthesis; promotes the secretion of FGF and PDGF by monocytes.

TGF-α (Transforming growth factor-α)—Stimulates mesenchymal, epithelial and endothelial cells.

EGF—(Epithelial Growth Factor)—Stimulates re-epithelialisation, the formation of new blood vessels and collagenase activity.

The PRP/fibrin glue composition or "cocktail" of the present invention is designed to have a viscosity that allows it to be injected at the repair site and to further adhere to the resurfaced tissue (bone, ligament or cartilage) and solidify within minutes, preferably within about 1 to about 5 minutes, more preferably within about 2 minutes. In particular embodiments, the PRP/fibrin glue composition or "cocktail" may be injected through a slot or channel of a biologic resurfacing mold (for example, a cap or a clear, plastic umbrella) that is placed over a prepared osteochondral socket and expanded to fully cover the diameter of the osteochondral socket. The PRP/fibrin glue mixture is injected through the channel or slot provided within the mold.

The use of the biological component/fibrin glue composition (preferably, PRP/fibrin glue composition) or "cocktail" of the present invention will be described below with reference to a particular application, i.e., an arthroscopic knee resurfacing application. However, the invention contemplates additional applications, for example, hip resurfacing, patella resurfacing, OATS resurfacing, among many other arthroscopic applications.

According to a method of osteochondral knee resurfacing of the present invention, an osteochondral socket is formed according to known methods in the art (for example, by employing a retrograde pin and retrograde cutter to prepare the socket bed). A biologic resurfacing mold or cap is inserted through an appropriate arthroscopic portal and placed over the prepared osteochondral socket. In exemplary embodiments, the biologic resurfacing cap may be a convex or concave metal cap, provided with an external handle to cover the defect (when inserted arthroscopically through an anteromedial portal and held securely over the defect).

Once the cap is fully inserted over the defect, a biologic cocktail of autogenous BMA/ACP/PRP options is mixed with fibrin glue and inserted with a syringe and needle through the tunnel (for example, the retrograde transosseus tunnel) into the defect. The cap molds the anatomical surface of the biologic cocktail until sufficient coagulation and solidification occurs within minutes, preferably about 1 to about 5 minutes, more preferably about 2 minutes. The cap may be removed and the process repeated for the tibia or other defects.

The cap may be also disposable and provided with a channel or slot through which the autogenous BMA/ACP/PRP options/ fibrin glue may be injected. Disposable biologic resurfacing caps may be manufactured at various handle angles (for example, 180 degree and 90 degree handle angles), as required by arthroscopy portals and defect locations. PRP solidified with fibrin glue is superior to microfracturing in osteochondral resurfacing. This option may be ideally indicated for treating trochlear groove osteochondral defects due to drilling angle flexibility.

In yet additional exemplary embodiments, the biologic resurfacing mold or cap may be a clear, plastic umbrella-like cap which is designed to expand (by resiliency) to the appropriate diameter and to be placed fully over the prepared socket. In this embodiment, the cap is introduced through the transosseous tunnel, at the defect site, through a cannula, for example. Once the outer tube of the instrument is retracted, a clear, plastic umbrella-like cap expands by resiliency to the appropriate diameter of the tunnel, allowing the cap to be placed fully over the prepared socket. Once the cap is fully set over the defect site, the biologic cocktail of autogenous BMA/ACP/PRP options is mixed with fibrin glue and inserted with a syringe and needle through cap into the tunnel to reach the defect. The clear, plastic umbrella has the appropriate concave undersurface to mold the biologic cocktail to the appropriate anatomic height, curvature and configuration in the defect during the solidification period of few minutes with arthroscopic viewing and injection control through the clear cap. The umbrella can be carefully articulated over the biologic repair to smooth out any remaining impinging areas prior to removal.

The present invention also provides a system for arthroscopic biologic osteochondral resurfacing. The arthroscopic resurfacing system includes a mixture or biococktail comprising ACP and/or PRP and/or BMA and fibrin glue, arthroscopic drill guides, cutters, and disposable products (for example, disposable molds or caps) for biologic resurfacing. The arthroscopic resurfacing system of the present invention may be employed in various resurfacing procedures such as hip resurfacing, patella resurfacing, OATS resurfacing, and femoral condyle focal defect resurfacing, among many other arthroscopic applications.

If ACP is employed, the ACP may be obtained from blood from the patient, which is separated using a centrifuge, for example, to retrieve certain healing components such as growth factors, to obtain the ACP. Preferably, the ACP has a platelet concentration factor of about 2 compared to the platelet concentration of the patient's normal blood. For example, the ACP may contain about 470,000 platelet/microliter (for a donor) compared to the about 200,000 platelet/microliter of the donor's whole blood, and compared to the about 500,000-1,000,000 platelet/microliter of the platelet-rich plasma (PRP) (of the donor), and compared to about 0 platelet/microliter of the platelet-poor plasma (PPP) (of the donor).

The ACP may also comprise autologous growth factors as defined above. In a preferred embodiment, the term "growth factor" includes autologous growth factors produced from a patient's own blood, obtained by a centrifugation process. Optionally, the ACP may comprise additional antiseptic chemicals and/or antibiotics and/or electrolytes. The additional antiseptics and/or the antibiotics and/or the electrolytes will typically be present in the plasma in a predetermined concentration range, which will be dependent upon the particular tissue site and application, as well as the specific activity of the antiseptic and/or the antibiotic and/or the electrolytes. The antibiotics may be selected from the group consisting of a Neosporin®, vancomycin and genamycin, and combinations thereof.

The ACP may further comprise one or more additional components which promote or enhance the wound healing effectiveness of the autologous growth factors. As such, hormones or site-specific hybrid proteins may be incorporated in the autologous blood suspension to maximize the availability of the autologous growth factors at the tissue to be repaired and/or to potentiate wound healing.

Figure 2:
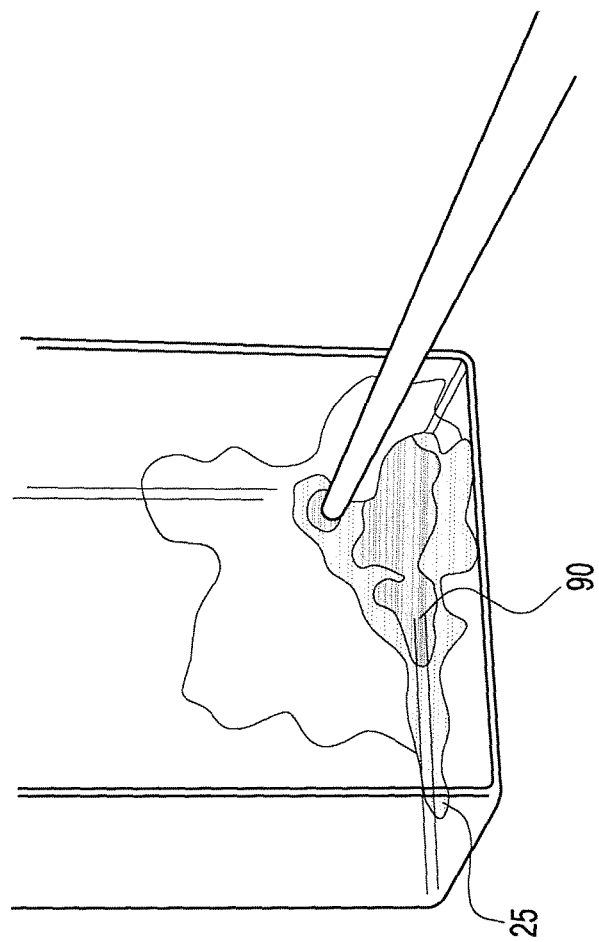
FIG. 2 illustrates the Fibrin glue of FIG. 1 added to ACP.

An exemplary method of producing fibrin glue (for example, Fibrine glue) mixed with ACP to establish a technique for the biologic component of the arthroscopic osteochondral resurfacing system is detailed below with reference to FIGS. 1-3. In an exemplary embodiment, the materials used in the method of the present invention comprise a Tissucol kit 1,0 Immuno 15 (from Baxter, for example) comprising fibrin glue 16 and illustrated in FIG. 1 in pre-packaged, ready-to-use form. The Tissucol Fibrine glue 16 is added to ACP plasma 25 (FIG. 2).

In an exemplary and illustrative embodiment only, the ACP plasma 25 was prepared from whole blood, by centrifugation of about 1500 rpm for about 5 minutes. Tissucol Fibrin glue 16 was prepared by using the low concentrated thrombin (L) leading to a slow solidifying glue. Approximately 2 ml ACP 25 were gently mixed with about 1 ml Tissucol 16 using a plastic rod, for example, to form ACP plasma/ Tissucol composition 90 (FIG. 2). After approximately 1 to 5 minutes, preferably about 2 minutes, a clot 100 (FIG. 3) of ACP plasma/ Tissucol was obtained.

Figure 3:
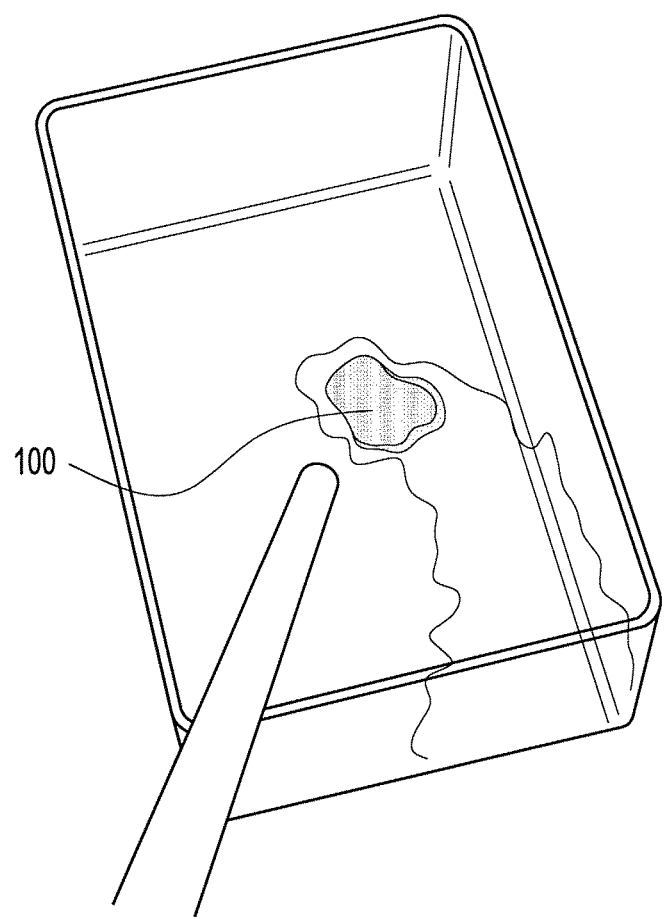
FIG. 3 illustrates a clot of Fibrin glue/ACP formed according to an embodiment of the present invention.
Figure 4:
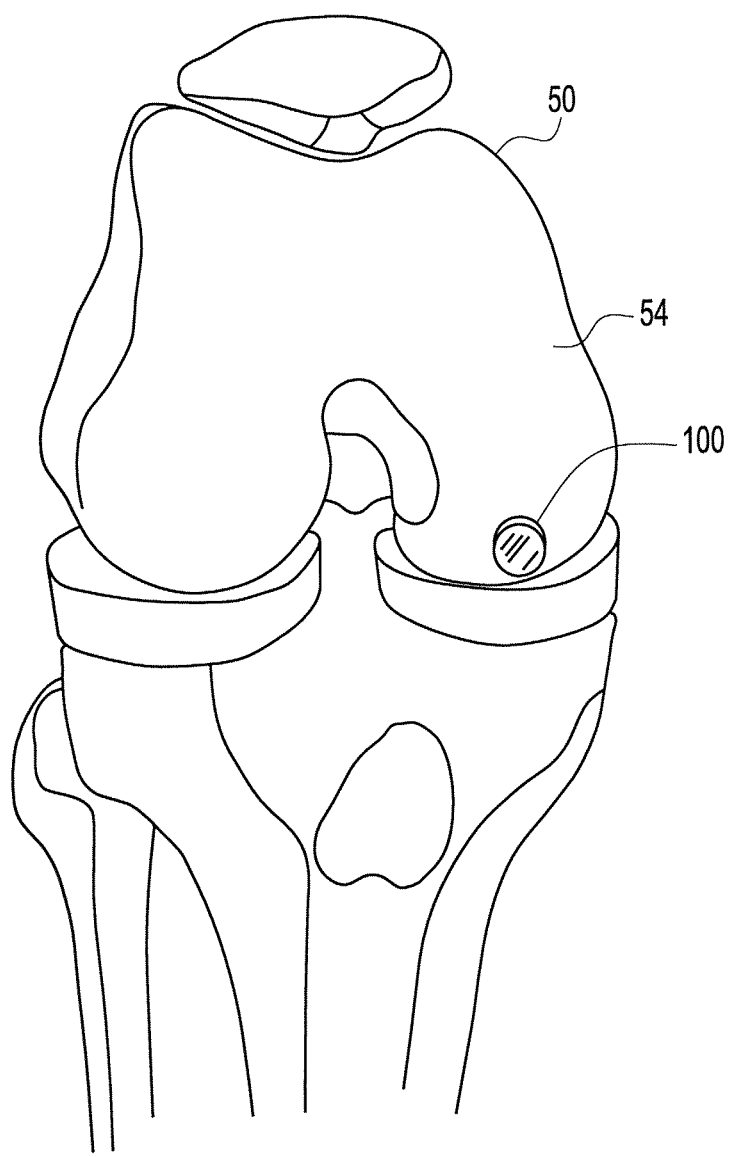
FIG. 4 illustrates a schematic view of a knee damage repair with the clot of FIG. 3 and in accordance with an embodiment of the present invention.

Clot 100 of FIG. 3 has the consistency of chewing-gum and no liquid could be pressed out. The surface of clot 100 is not sticky. The clot 100 may be designed with an optimal ACP/Tissucol ratio. The clot may be inserted in the vicinity of a cartilage defect (or directly in a cartilage defect) and may be sealed with pure and rapid solidifying glue such as Tissucol Fibrin glue. For example, FIG. 4 illustrates a schematic view of knee 50 with damaged site 54 (for example, cartilage defect 54) that undergoes osteochondral resurfacing with exemplary clot 100 of the present invention. As illustrated in FIG. 4, clot 100 is provided directly over the cartilage defect or repair site 54, to advance the healing of the damaged tissue and tissue growth. Alternatively, and as detailed above, clot 100 may be inserted in a bone tunnel or bone socket provided at the repair site 54 and prior to insertion of an osteochondral core, if desired.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of arthroscopic osteochondral resurfacing treatment comprising:
    contacting a mixture comprising fibrin glue and a biological component to a cartilage defect at an arthroscopically resurfaced osteochondral site,
    wherein the mixture is injected through a channel, slot, or inner hole of a resurfacing cap positioned over the defect, and
    wherein the resurfacing cap is delivered to the defect site in an arthroscopic portal and comprises an undersurface similar to the surface of the resurfaced site and is configured to resiliently expand over the defect after delivery to the defect site; and
    contacting the undersurface of the resurfacing cap to the mixture until solidification of the mixture.

2. The method of claim 1, wherein the biological component is selected from the group consisting of platelet rich plasma (PRP), bone marrow aspirate, and combinations thereof.

3. The method of claim 2, wherein the biological component is PRP.

4. The method of claim 2, wherein the biological component further comprises a growth factor, antiseptic, antibiotic, electrolyte, or combinations there.

5. The method of claim 4, wherein the growth factor is selected from the group consisting of platelet-derived growth factor, fibroblast growth factor, transforming growth factor-α, transforming growth factor-β, epithelial growth factor, and combinations thereof.

6. The method of claim 1, wherein the solidification of the mixture occurs in about 1 to about 5 minutes.

7. The method of claim 1, wherein the solidification of the mixture occurs in about 2 minutes.

8. The method of claim 1, wherein the resurfacing cap is metal.

9. The method of claim 1, wherein the resurfacing cap is plastic.

10. The method of claim 9, wherein the plastic resurfacing cap is clear.

11. The method of claim 9, wherein the plastic resurfacing cap is umbrella-shaped.

12. A method of arthroscopic osteochondral resurfacing treatment comprising:
    contacting a mixture consisting of fibrin glue and a biological component to a cartilage defect at an arthroscopically resurfaced osteochondral site,
    wherein the mixture is injected through a channel, slot, or inner hole of an umbrella-shaped resurfacing cap positioned over the defect, and
    wherein the resurfacing cap is delivered to the defect site in an arthroscopic portal and comprises an undersurface similar to the surface of the resurfaced site and is configured to resiliently expand over the defect after delivery to the defect site; and
    molding an anatomical surface by contacting the undersurface of the resurfacing cap to the mixture until solidification of the mixture.

13. The method of claim 12, wherein the biological component is selected from the group consisting of platelet rich plasma (PRP), bone marrow aspirate, and combinations thereof.

14. The method of claim 12, wherein the biological component is PRP.

15. The method of claim 12, wherein the solidification of the mixture occurs in about 1 to about 5 minutes.

16. The method of claim 12, wherein the solidification of the mixture occurs in about 2 minutes.

* * * * *